United States Patent
Cohen et al.

[19]

[11] Patent Number: 5,881,956
[45] Date of Patent: Mar. 16, 1999

[54] MICRODISPENSING OPHTHALMIC PUMP

[75] Inventors: Ben Z. Cohen, 140 E. 80th St., New York, N.Y. 10021; Nigel B. Kelly, New York, N.Y.

[73] Assignee: Ben Z. Cohen, New York, N.Y.

[21] Appl. No.: 694,206

[22] Filed: Aug. 8, 1996

[51] Int. Cl.[6] .................................................. A62C 11/00
[52] U.S. Cl. ..................... 239/333; 239/590; 222/321.7; 222/385
[58] Field of Search ..................... 239/331, 333, 239/590, 590.5; 222/321.1, 321.7, 321.9, 322, 383.1, 385, 341; 604/289, 290, 296; 606/107

[56]  References Cited

U.S. PATENT DOCUMENTS

| | | | |
|---|---|---|---|
| 3,223,292 | 12/1965 | Keeney et al. | 222/321 |
| 3,844,452 | 10/1974 | Blum | 222/321 |
| 4,140,249 | 2/1979 | Majima | 222/321 |
| 4,185,776 | 1/1980 | Nozawa | 239/333 |
| 4,305,530 | 12/1981 | Nozawa | 222/321 |
| 4,371,097 | 2/1983 | O'Neill | 222/321.9 |
| 4,607,765 | 8/1986 | Ruscitti | 222/321.9 |
| 4,941,598 | 7/1990 | Lambelet, Jr. et al. | 222/321 |
| 5,152,435 | 10/1992 | Stand et al. | 222/341 |
| 5,579,958 | 12/1996 | Su | 222/321.7 |
| 5,630,793 | 5/1997 | Rowe | 604/289 |
| 5,649,649 | 7/1997 | Marelli | 222/321.1 |

FOREIGN PATENT DOCUMENTS

WO 96/00050  1/1996  WIPO .

*Primary Examiner*—Andres Kashnikow
*Assistant Examiner*—Lisa Ann Douglas
*Attorney, Agent, or Firm*—Anthony J. Casella; Gerald E. Hespos; Ludomir A. Budzyn

[57] ABSTRACT

A microdispensing ophthalmic pump is provided for repeatedly delivering doses as small as 5 microliters within an angular operating range. The pump basically comprises a reservoir, a dispensing cap, an actuator and a pump body with a pump mechanism disposed therein. The pump mechanism is regulated by a limited-travel inlet check valve and a biased-closed outlet check valve. A failsafe mechanism is formed between the actuator and dispensing cap to prevent operation of the pump outside the operating range.

35 Claims, 11 Drawing Sheets

MICRODISPENSING OPHTHALMIC PUMP

BACKGROUND OF THE INVENTION

1. Field of the Invention

This invention relates to a fluid medicine delivery device, and, more particularly, the invention is directed to a microdispensing ophthalmic pump for delivering a microdose of ophthalmic fluid.

2. Description of the Prior Art

U.S. Pat. No. 5,152,435 (hereinafter "the '435 patent)", entitled "OPHTHALMIC DISPENSING PUMP", discloses a manually operated dispensing pump capable of delivering a precise quantity of ophthalmic solution to the surface of an eye in a desired spray pattern with an impact pressure on the eye that is comfortably tolerable by an individual and was issued to a co-inventor, Ben Z. Cohen, of this patent. The '435 patent is incorporated by reference herein, including the extensive discussion of the shortcomings of the prior art. The spray pump of the '435 patent is a substantial improvement over the prior art, capable of delivering doses of ophthalmic fluid such as 50 microliters in the previously described manner. However, often a dose of much less than 50 microliters of ophthalmic fluid may be required to be delivered in the manner described above. Since a reduction in the size of a dosage inherently decreases the impact force exerted by the dose onto an eye, the administration of fluid by the '435 patent would be even more comfortably tolerable than that disclosed therein with a reduction in the size of the dose the '435 pump could deliver. Also, some medications can have toxic effects, even at doses as small as 50 microliters, and so doses of less than 50 microliters would be better tolerated.

It is a primary object of the subject invention to provide a manually operated microdispensing pump for delivering a microdose of ophthalmic solution as small as 5 microliters.

Also, it is an object of the subject invention to provide a manually operated microdispensing pump capable of repeatedly administering a full and proper microdose as small as 5 microliters.

SUMMARY OF THE INVENTION

The above-mentioned objects of the present invention are achieved by a new and improved manually operated microdispensing pump for delivering ophthalmic fluid. In particular, the new and improved manually operated microdispensing pump will enable an individual to repeatedly deliver a predetermined microdose of ophthalmic fluid.

In the preferred embodiment, the microdispensing pump of the subject invention is formed to be substantially cylindrical with one end being formed as a reservoir for storing the ophthalmic fluid intended to be dispensed. A pump body is threadedly secured to the reservoir with a cylindrical inner body formed therein which projects along a central axis into the reservoir. A dip tube is provided to communicate fluid from the reservoir to the inner body of the pump body. A pump mechanism is disposed within the inner body which urges fluid from the reservoir and through the pump of the subject invention. The pump mechanism comprises an inlet check valve element for regulating the flow of the fluid from the reservoir into the inner body, a cylindrical piston slidably disposed and sealingly supported within the inner body, an elongated poppet extending from the inner check valve element and through the inner body in a spatial relationship with the piston, an outlet check valve element for regulating flow of the fluid out of the inner body and a spring for urging the cylindrical piston into an upward position in contact with a head formed on the end of the poppet opposite the inlet check valve element.

The microdispensing pump of the subject invention further comprises a dispensing cap mounted onto the cylindrical piston and formed with an outlet chamber which communicates with the inner body, the communication therebetween being controlled by the outlet check valve element, and a slender discharge nozzle communicating the outlet chamber with the periphery of the dispensing cap. An actuator is slidably disposed adjacent the dispensing cap and substantially within the pump body.

Once primed with ophthalmic fluid within the inner body, the pump dispenses ophthalmic fluid with a downward translation of the actuator, the dispensing cap and the piston within the inner body. As the piston translates within the inner body, the volume therein is decreased with an accompanying increase in pressure of the ophthalmic fluid contained within the inner body. The check valve elements are both normally closed and contribute to the pressure build-up of the fluid. Eventually, the compressed ophthalmic solution will force the outlet check valve element open, thereby allowing fluid to enter the outlet chamber and the discharge nozzle and force out fluid previously drawn therein. The fluid is delivered in a non-aerosolized jet stream as a series of droplets. A spring is provided to urge the outlet check valve element into a closed position quickly after being forced open. The piston, having completed its downward translation, translates upward into contact with the head of the poppet due to the urging of the spring acting on the piston. As the piston comes into contact with the head of the poppet, the volume within the inner body is increased and the accompanying pressure decreased. The reduction of pressure within the inner body creates a suction effect which urges the inlet check valve element into an open position and draws fluid from the reservoir into the inner body. As pressure builds within the inner body due to the added fluid, the inlet check valve element will be urged into a closed position allowing the pump mechanism to be used again.

The new and improved manually operated microdispensing pump of the subject application uses a spring biased outlet check valve element and a limited-travel inlet check valve element to operate under the negligible pressures and strokes associated with the delivery of microdoses of fluid. In the preferred embodiment, a spring is applied to a stainless steel ball to form the outlet check valve, which is biased to a normally closed position. The suction created by the pump mechanism to draw fluid therein may affect the microdose of the pump if fluid disposed in the nozzle and the outlet chamber is drawn into the inner body due to the suction effect. During operation of the pump, the spring urges the outlet check valve element into a closed and seated position prior to suction being created in the inner body and ensures that a proper and full microdose of the ophthalmic fluid is maintained within the nozzle and the outlet chamber, unaffected by the suction effect.

An inlet check valve element is provided to regulate the flow of ophthalmic fluid into the pump of the subject invention. Since the delivery of microdoses as small as 5 microliters involves a negligible stroke of the inlet check valve element, a protrusion is disposed opposite the inlet check valve element which restricts the check valve element's range of motion and prevents the check valve element from simply shuttling during usage. The motion of the inlet check valve element is limited so that in an open position the volume displaced by the inlet check valve element in travelling from a closed position to an open position is less than the volume of the dose being dispensed by the pump. In the preferred embodiment, this volume is the swept volume of an inlet check valve ball and is calculated by taking the product of the clearance between the inlet check valve ball and the protrusion times the cross-sectional area of the inlet check valve ball: (clearance) $\times[\pi\times(\text{radius of the ball})^2]$. Although a ball is preferred, any shape inlet check valve element may be used, such as a disk, with the swept volume being determined by the product of the clearance between the inlet check valve element and the protrusion times the largest cross-sectional area of the inlet check valve element measured in a plane perpendicular to the flow of fluid through the check valve. Thus, one feature of the new and improved manually operated microdispensing pump of the subject invention is a valve arrangement sensitive to the negligible strokes associated with microdosing.

Prior to initial use, the pump of the subject invention must be primed, wherein air is expelled from the pump mechanism. The pump is primed through the repeated actuation of the pump mechanism which draws fluid therein and forces air thereout. After priming, the re-introduction of air into the pump mechanism is undesired, since air pockets may be formed within the pump mechanism which may render the pump mechanism inoperative. To prevent the entrapment of air within the pump mechanism, the pump of the subject invention includes a failsafe device, a limited volume dip tube and a spherical inlet chamber which function to prevent the introduction and entrapment of air bubbles into the pump mechanism. The failsafe device comprises a ball disposed within an arcuate slotted track formed in the dispensing cap, which cooperates with an actuating block extending from the actuator. To operate the pump of the subject invention, the actuator is urged towards the dispensing cap with the actuating block coming into contact and pressing against the ball disposed within the track, which, under further urging, depresses the dispensing cap and activates the pump mechanism. If the pump were to be operated with the opening of the dip tube exposed to air entrapped within the reservoir, air could possibly be introduced into the pump mechanism. The slot of the failsafe device is formed to guide the ball out of alignment with the actuating block when the dip tube is positioned to be in communication with air trapped in the reservoir, with the ophthalmic fluid being within a predetermined range of fluid levels. Preferably, the slot is formed to allow the pump of the subject invention to operate with the nozzle discharge positioned in a range from approximately 155 to 290 degrees, going clockwise. Outside of this range, the ball will slide within the arcuate slot and prevent actuation of the subject invention pump.

To limit the entrapment of air in the pump during priming, the inlet chamber is formed to be substantially spherical to avoid the creation or entrapment of air bubbles therein. Also, during priming, as the pump is actuated with the inlet check valve element not being encompassed by ophthalmic fluid, the inlet check valve element will not provide an adequate seal against its seat and will allow fluid to freely pass the check valve element into the dip tube. This leakage, when the inlet check valve element is in a dry state, may cause an air pocket in the dip tube which prevents ophthalmic fluid from entering the pump mechanism. The air pocket will react to the actuation of the pump by rising and falling within the dip tube corresponding to the existence of suction within the pump mechanism. As a result, ophthalmic fluid is prevented from being drawn into the pump mechanism. To avoid such a problem, the dip tube of the pump of the subject invention is formed to encompass a volume less than the microdose intended to be dispensed by the pump to ensure that the inlet check valve element is submersed in ophthalmic fluid, since the inlet check valve element will not leak when encompassed by ophthalmic fluid. The dip tube has a hollow, substantially cylindric center which contains fluid from its free end to the seat of the inlet check valve element, which will be fully drawn into the pump upon a single actuation. Limiting the volume of the dip tube below the microdose of the pump ensures sufficient fluid will be drawn from the dip tube with a single actuation of the pump which will encompass the inlet check valve element and prevent the formation of an air pocket in the dip tube. Thus, another feature of the new and improved manually operated microdispensing pump of the subject invention prevents the entrapment of air within the pump mechanism.

To ensure proper operation of the pump, an annular tapered latch, formed from a resilient plastic, is provided at the base of the actuator and disposed about the inner body and pump mechanism. A corresponding annular shoulder is formed about the inner body with a top surface which comes into contact with the bottom surface of the latch with the downward translation of the actuator. The actuator can translate downward till the bottom surface of the latch is in contact with the annular shoulder without the pump dispensing any fluid. The actuator can further translate downwards, with the latch freely deforming. As the latch continues to deform, the latch generates resistance to further downward translation requiring increasing force to accomplish such translation. The increase in force will eventually build up and overcome a predetermined threshold force, which causes the latch to yield with a great reduction in resistance to even further downward translation.

To dispense fluid from the pump, a threshold force must be applied to deform the latch and exceed the yield point, thereby allowing the actuator translation into the pump body such that the pump mechanism is activated through the dispensing cap. The force needed to overcome the latch is much greater than that required to drive the piston a required stroke. Once the latch is overcome, the threshold force will cause the piston to rapidly travel its full stroke. A full and proper dose, as predetermined by the stroke of the pump mechanism, will be ensured through the elimination of a partial pump stroke. Therefore, another feature of the new and improved manually operated microdispensing pump of the subject invention is a latch for ensuring proper dosing.

Also, the translation of the dispensing cap into the pump body results in the compression of air trapped therebetween and resistance to downward translation. Vents may be provided to allow the compressed air to escape. The combination of the latch and the vents can be used to establish a threshold force needed to operate the subject invention. The quantity and the size of the vents can be manipulated to add or decrease the threshold force needed to overcome the latch.

The deformation of the latch converts the threshold force needed to deform the latch into a rapid actuation of the pump mechanism. An operator of the new and improved pump of the subject invention will not sense the point at which the latch will deform and will continue to apply the threshold force after deformation of the latch. Once deformed, the latch provides no resistance to further translation of the actuator and dispensing cap, which under the applied threshold force will rapidly move and activate the pump mechanism. This rapid activation will cause the pump mechanism to dispense fluid in a non-aerosolized jet stream as a series of droplets which will hit the desired target nearly simultaneously. As an additional feature, the rapid translation of the dispensing cap within the pump body causes the dispensing cap to strike the pump body, which limits the translation of the dispensing body, such that an audible click, tactile click, or any combination thereof, is generated. The audible or tactile click indicates to a user of the subject invention that a dose has been administered. The audible click can be avoided by padding the point of contact either on the dispensing cap or the pump body with a cushioning material, such as rubber or laminated paper.

The latch is not necessary to create a jet stream, if the pump can be actuated quickly without it. However, the latch ensures the pump mechanism will be activated with sufficient velocity to create a jet stream. Thus, yet another feature of the new and improved manually operated microdispensing pump of the subject invention is a deformable latch which ensures delivery of fluid from the pump in a jet stream.

As with all medical dispensers, precautions must be taken to prevent the introduction of foreign matter which could cause contamination of the dispenser. The spring acting against the outlet check valve element prevents the introduction of foreign matter into the pump mechanism. During fluid administration, the inner body draws fluid through the dip tube as fluid is dispensed. The drawing effect not only affects the inlet check valve element, but also the outlet check valve element. The spring urges the outlet check valve element into a seated position prior to suction being created within the inner body and prevents the drawing of contaminants into the pump through the nozzle.

Also, the dispensing cap, along with the discharge nozzle, is disposed within the actuator during non-use. In this position, the nozzle is protected from dirt and debris. The mouth of the discharge nozzle is provided with a conical rim which aids in the separation of the discharging fluid from the nozzle. The rim is encompassed by an annular depression which provides a pocket for collecting undispensed fluid. The annular depression is recessed within the dispensing cap and provides for separation of undispensed fluid from the nozzle, thereby avoiding possible blockage, and from the actuator, thereby avoiding possible gumming on the actuator of undispensed fluid which could contaminate future doses.

Although the discussion of the subject invention refers to ophthalmic solutions and administration to a person's eye, the new and improved manually operated microdispensing pump of the subject invention can be used with any type of fluid, such as lubricants, fragrances, medications and so on, for which a microdose as small as 5 microliters may be required.

These and other features of the invention will be better understood through a study of the following detailed description of the invention and the accompanying drawings.

DETAILED DESCRIPTION OF THE PREFERRED EMBODIMENTS

Figure 1:
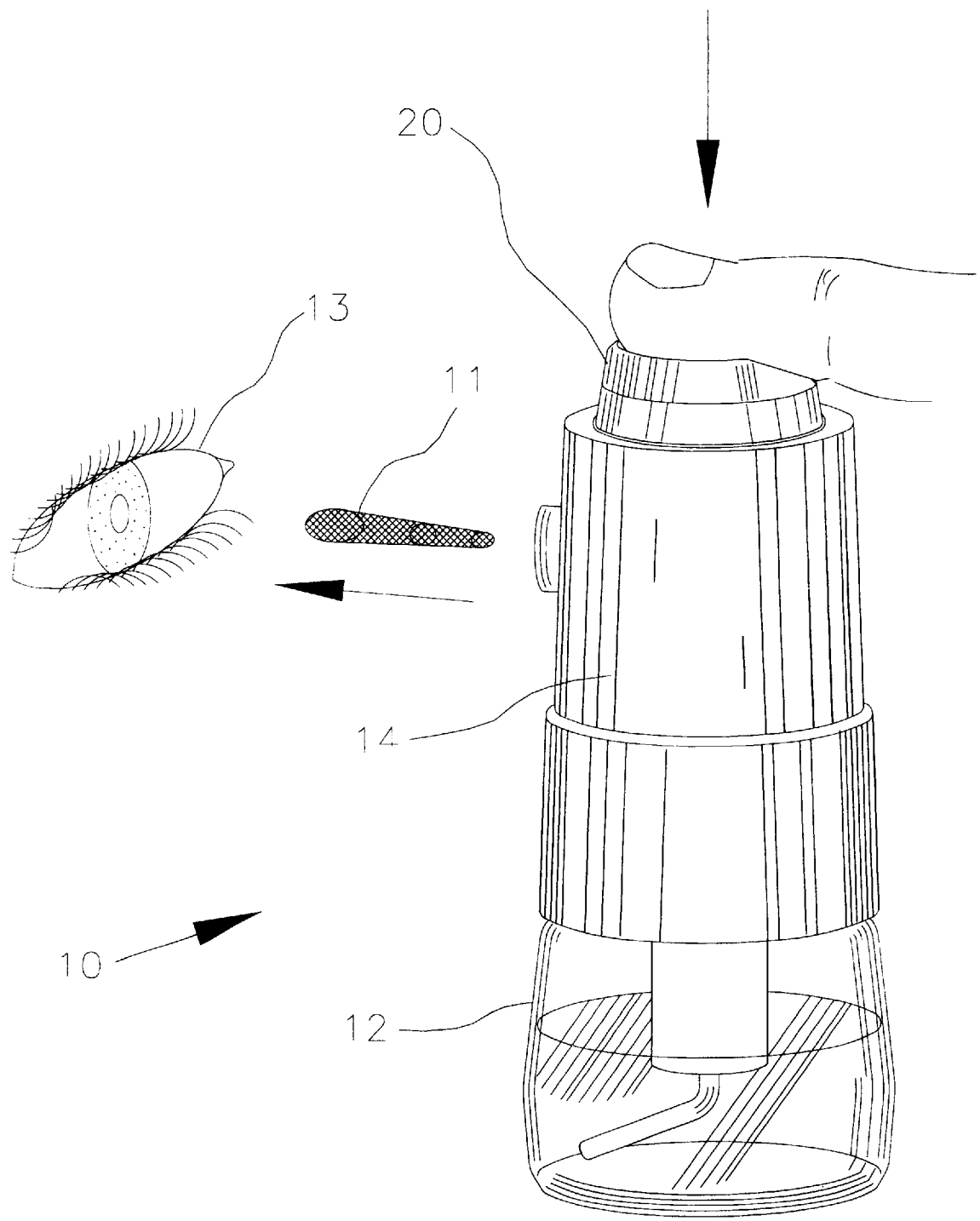
FIG. 1 is a perspective view of the new and improved pump of the subject invention.

As shown in FIG. 1, the new and improved manually operated microdispensing pump of the subject invention is generally indicated by reference numeral 10 and is capable of delivering a microdose of ophthalmic fluid 11 to a human eye 13. Referring generally to FIGS. 1–5, the pump 10 comprises a reservoir 12, a pump body 14, a pump mechanism 16, a dispensing cap 18 and an actuator 20.

The reservoir 12 is generally cup-shaped and formed to accommodate fluid. The pump body 14 is mounted onto the reservoir 12 and secured thereto through threaded engagement of threads 22, formed on neck 24 of the reservoir 12, and threads 26, formed on a lower portion 28 of the pump body 14 which is disposed about the neck 24. An annular seal 25 is disposed between the pump body 14 and the reservoir 12 which prevents fluid from leaking through the threads 22, 26. The pump body 14 comprises a substantially cylindrical outer shell 30, a substantially cylindrical inner body 32 disposed co-axially within the outer shell 30, and a transverse bulkhead 34 joining the two cylindrical elements. The outer shell 30 is formed to define a dispensing aperture 36 with sight 38 disposed thereabout. The sight 38 allows a user of the pump 10 to aim and direct the pump's discharge.

The inner body 32 extends from both sides of the bulkhead 34 with one end 40 being open, an opposed end 42 having an inlet channel 44 and an inlet check valve seat 46 formed therein, and a cylindrical inner chamber 48 extending between the two ends 40, 42. A hook-shaped guide 50 depends from the lower end of the inner body 42 onto which dip tube 52 is mounted. The guide 50 directs the dip tube 52, which encompasses a volume less than the microdose 11, to the edge of the reservoir 12 in alignment with the sight 38. The guide 50 and the dip tube 52 allow an individual to efficiently draw fluid from the reservoir 12, since the dip tube 52 is fixed and formed to reach deep into the reservoir 12 and communicate with very low levels of fluid. Furthermore, an individual has a tendency to tilt a dispenser forward in administering a fluid; the guide 50 and an end of the dip tube 54 are aligned to consider this tendency.

A cylindrical piston 56 is slidably disposed within the inner chamber 48 with an annular seal 58 being in contact with the surface of the inner chamber 48. The piston 56 is formed with a cylindrical inner surface 55 having a constant cross-section and a top end 57 forming an opening smaller than the cross-section of the inner surface 55. A poppet 60 is located within the piston 56 and extends throughout the inner chamber 48. The poppet 60 is formed with a base 62 having a hemispherical lower surface 64, which together with the inlet check valve seat 46 form a generally spherical inlet chamber 66. The inlet channel 44 communicates with the inlet chamber 66 and together with the dip tube 52 form a passageway for fluid to pass into the pump body 14. An inlet check valve element 67, preferably a ball, is seated in the inlet check valve seat 46 within the inlet chamber 66. A protrusion 68 extends from the lower surface 64 of the poppet 60 into close proximity with the inlet check valve element 67. The protrusion 68 limits the travel of the inlet check valve element 67 within the inlet chamber 66 so that the swept volume of the inlet check valve element 67 is less than the microdose 11, calculated in a manner previously described.

A stem 69 extends from the base 62 through the piston 56 in a spatial relationship, thereby forming an annular flow path 70 therebetween. A head 72 depends from the stem 69 and has a diameter greater than the inner diameter of the piston 56. A spring 74 is disposed about the base 62 of the poppet 60, and urges the top of the piston 57 into sealing contact with the head 72. The inner chamber 48 and the annular flow path 70 receive fluid from the inlet chamber 66 through ports 76 formed in the base of the poppet 62. An outlet check valve housing 77 is mounted to the piston 56 with a tapered portion 78 being formed therein. The poppet 60 is disposed within the piston 56 by forcing the head 72 through the piston 56. The piston 56 is preferably made from low density polyethylene, which will allow the head 72, preferably made from high density polyethylene, to pass through the piston 56 without permanent deformation.

Figure 2:
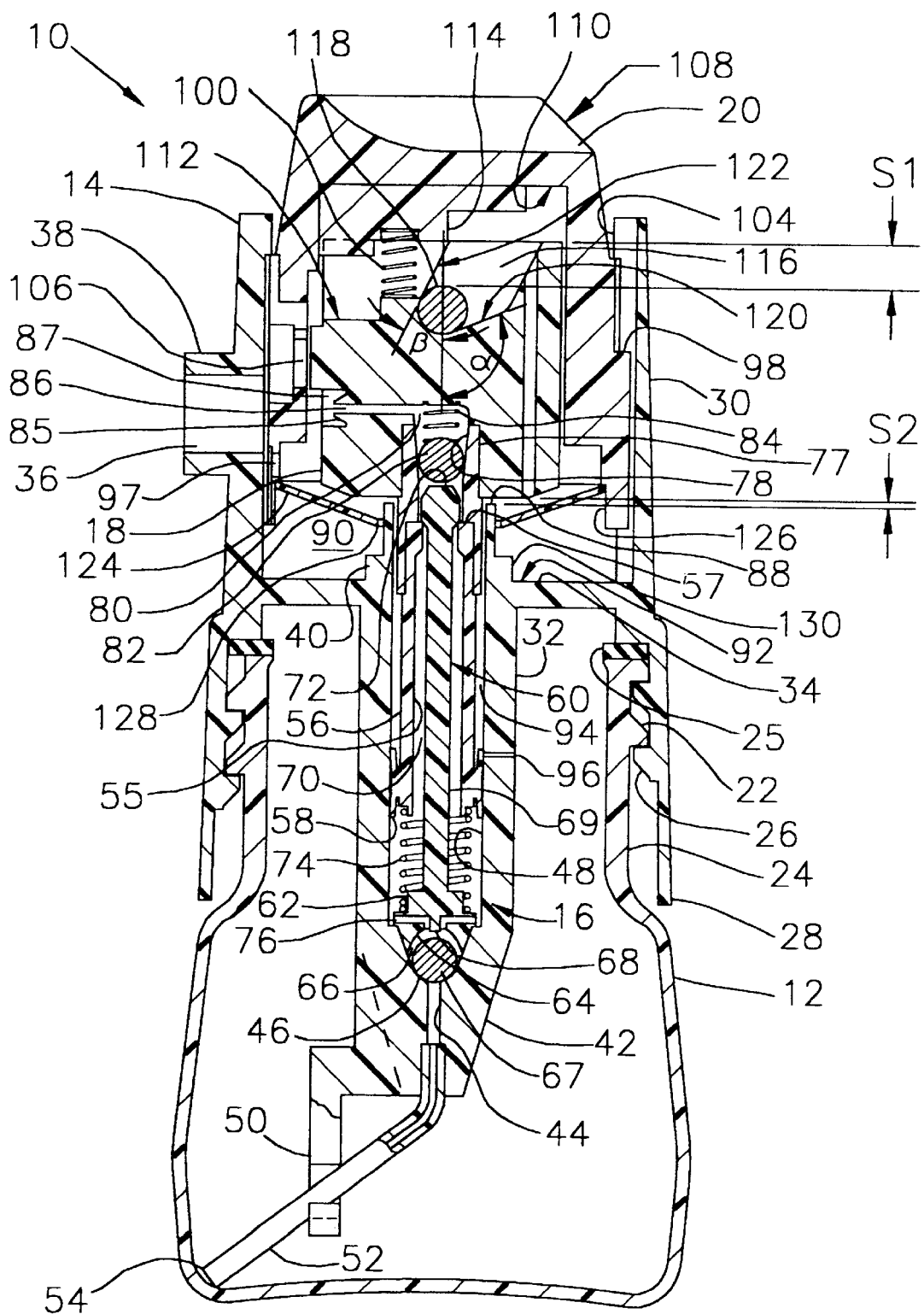
FIG. 2 is a cross-sectional view of the new and improved pump of the subject invention in an unactuated position.
Figure 6:
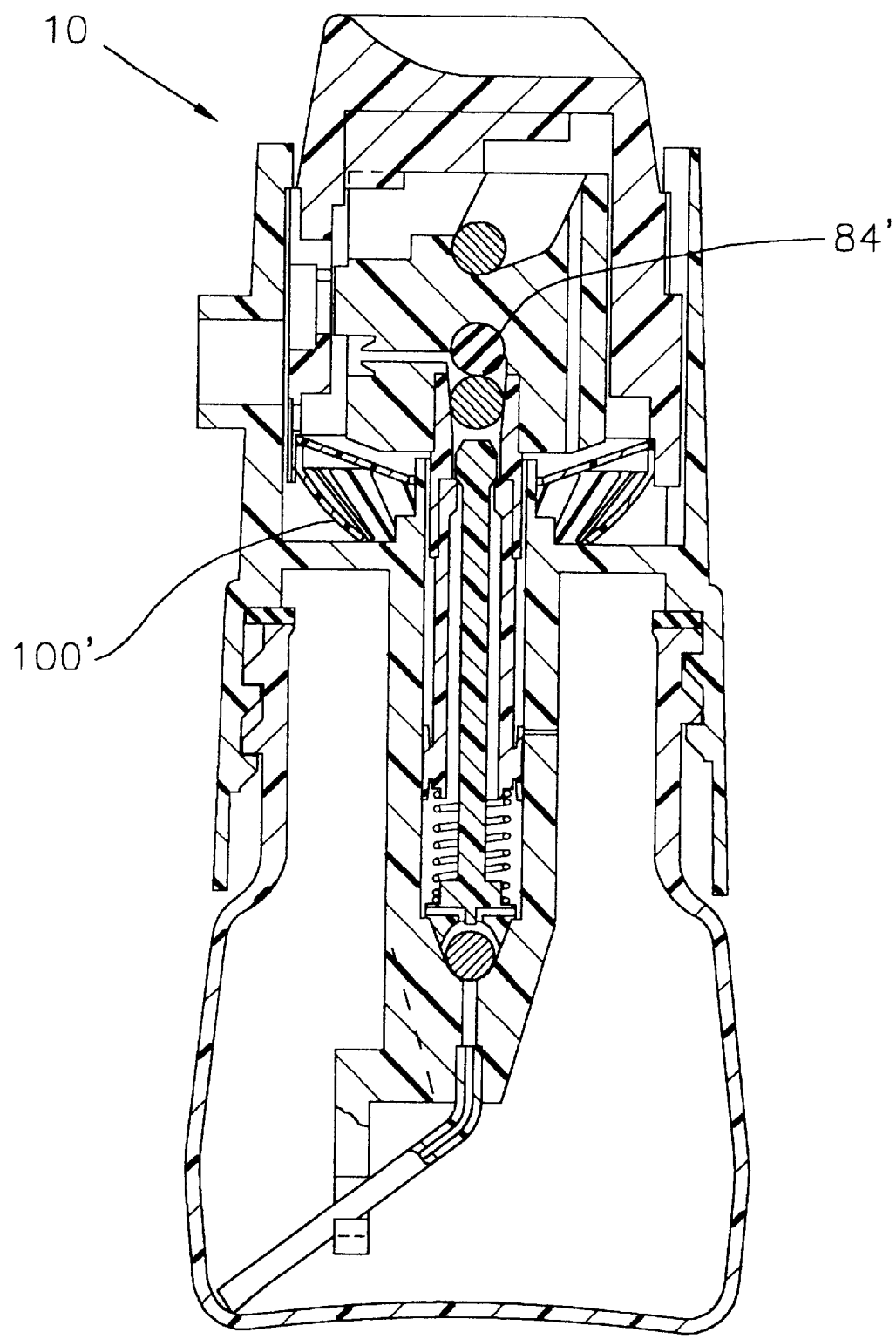
FIG. 6 is a cross-sectional view of an alternative embodiment of the new and improved pump of the subject invention.
Figure 7:
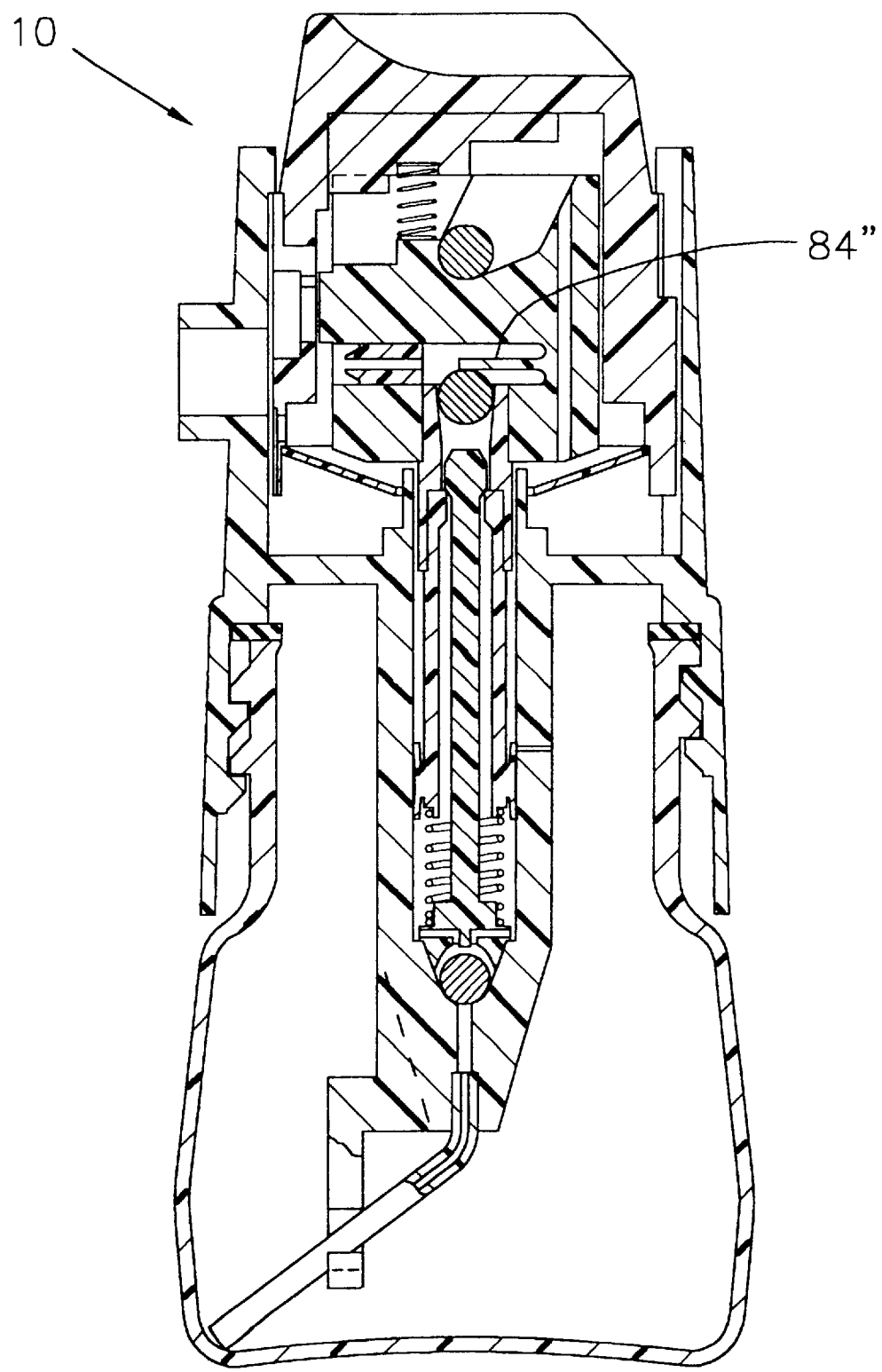
FIG. 7 is a cross-sectional view of an alternative embodiment of the new and improved pump of the subject invention.

The dispensing cap 18 is mounted onto the outlet check valve housing 77. An outlet chamber 80 is formed within the dispensing cap 18 and communicates with the annular flow path 70 when the head 72 is not in contact with the piston 56. An outlet check valve element 82, preferably a ball, is located within the outlet chamber 80 and limits flow from the annular flow path 70 into the outlet chamber 80. A quick return biasing means 84 urges the outlet check valve element 82 into sealing contact with the tapered portion 78. Preferably, the quick return biasing means 84 is comprised of a conventional coil spring with a spring force of 2.9 lbs/in., as shown in FIG. 2. Alternatively, a resilient rubber ball 84' or cantilevered latch spring 84" can also be used, as shown in FIGS. 6–7.

A straight walled discharge nozzle 86 is formed to communicate the outlet chamber 80 with the periphery of the dispensing cap 18. The discharge nozzle 86 is preferably formed to define a length to throat ratio of approximately 7 to 1. The design of the slender discharge nozzle 86 contributes to the formation of a jet stream which is dispensed therefrom. The nozzle 86 is formed with a conical rim 85 and an annular depression 87 about the discharge at the periphery of the dispensing cap 18. The conical rim 85 aides in the formation of a jet stream which discharges from the nozzle 86 by causing separation of the fluid from the dispensing cap 18 since little surface area is provided about the discharge of the nozzle 86 to which fluid can adhere. If any fluid does adhere, the undispensed fluid collects in the annular depression 87. The annular depression 87 allows undispensed fluid to collect which will not adhere to the discharge of the nozzle 86, possibly causing blockage, or to the actuator 20, possibly causing gumming and contamination of later doses.

An upper surface 88 of the inner body 32 and the head of the poppet 72 limit the stroke of the piston 56. The upper surface 88 represents the lower limit of the stroke whereas the head 72 represents the upper limit. The amount of the microdose can be controlled through the establishment of these limits.

A void 90 exists between the upper surface 92 of the bulkhead 34 and the dispensing cap 18. The void 90, annular air chamber 94, air vents 97 and vent 96, formed within the wall of the inner body 32, create an atmospheric flow path through which ambient pressure is exposed to the surface of the fluid when the piston 56 is not in contact with the head 72. The introduction of ambient pressure into the reservoir 12 ensures the surface of the fluid will be under atmospheric pressure and drawn into the dip tube 52 due to a drop in pressure in the inlet chamber 66, as described below. The reservoir 12 cannot be filled so that the vent 96 is covered by fluid, which would prevent the introduction of atmospheric pressure. The void 90 is vented to atmosphere by the air vents 97. The air vents 97 also provide pathways for air to escape from the void 90 when the actuator 20 is depressed into the pump body 14 which compresses the air found in the void 90.

Figure 3:
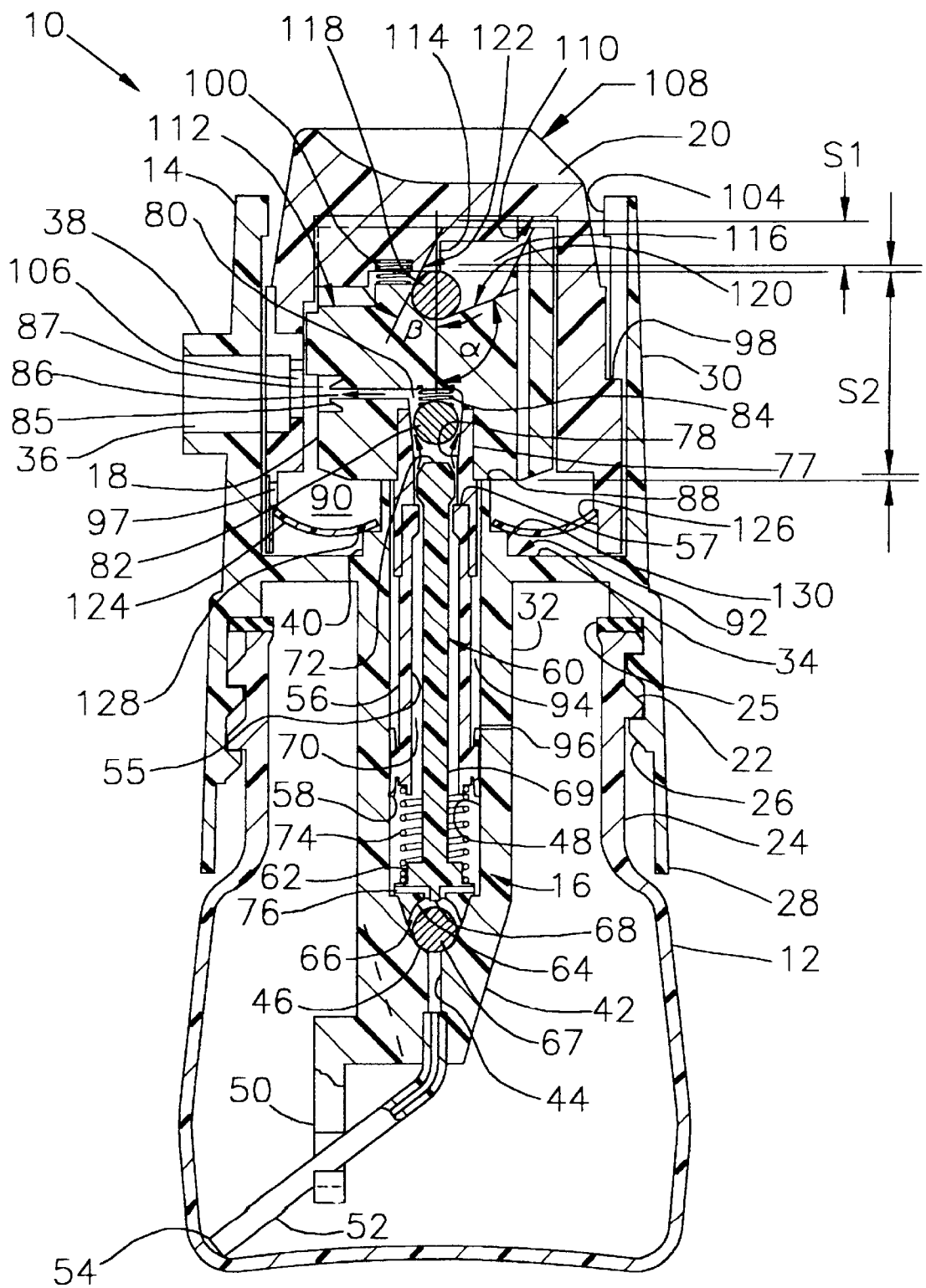
FIG. 3 is a cross-sectional view of the new and improved pump of the subject invention in a dispensing position.
Figure 9A:
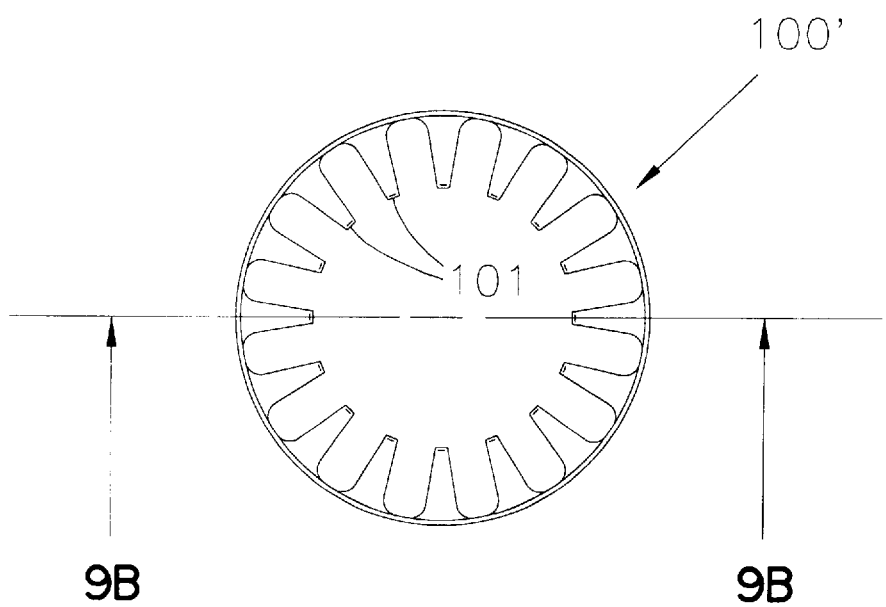
FIGS. 9A–B are respectively is a plan and cross-sectional side view of the spring fingers of an alternative embodiment of the subject invention.
Figure 9B:
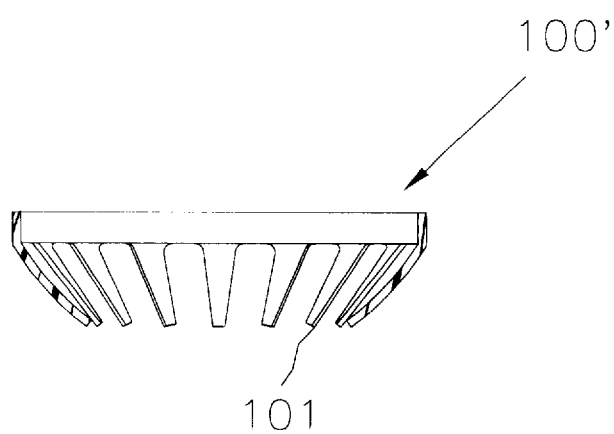
Figure 10A:
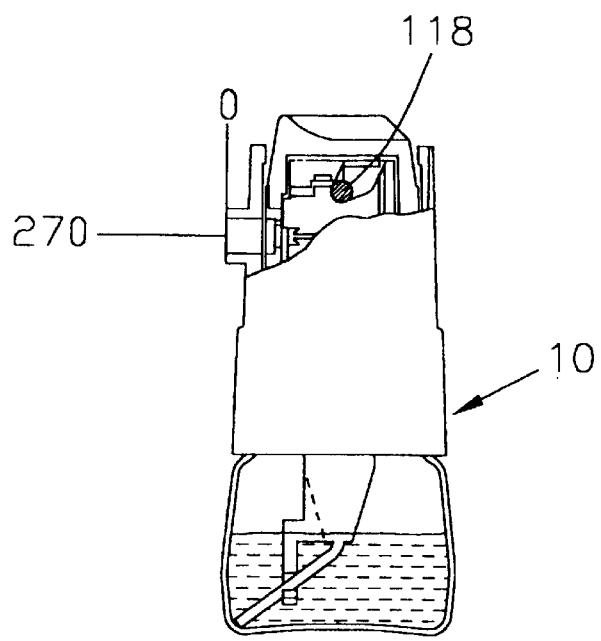
FIGS. 10A–D are cross-sectional views of the operating range of the new and improved pump of the subject invention.
Figure 10B:
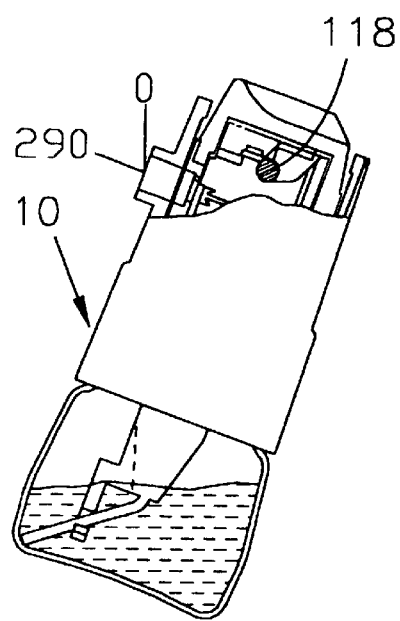
Figure 10C:
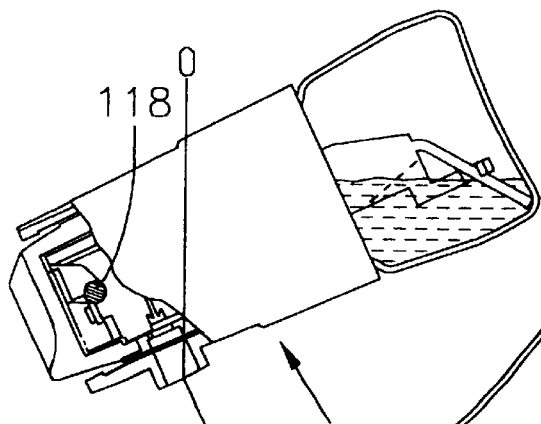
Figure 10D:
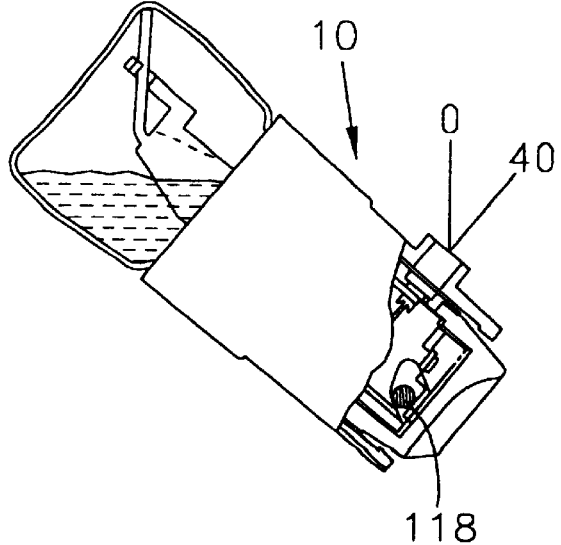
Figure 11A:
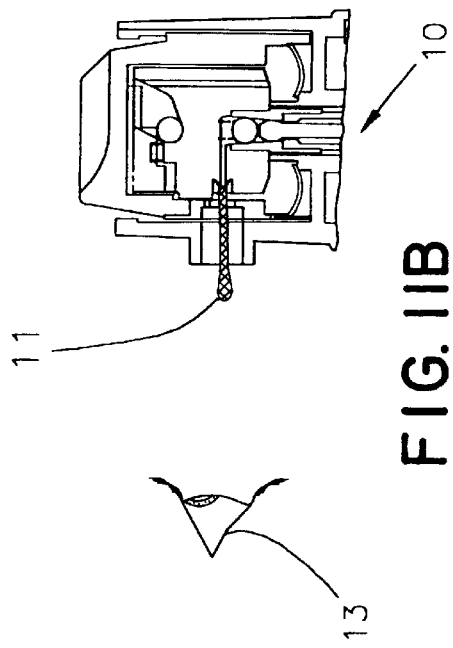
FIGS. 11A–D are cross-sectional views of the jet stream dispensed by the new and improved pump of the subject invention.
Figure 11B:
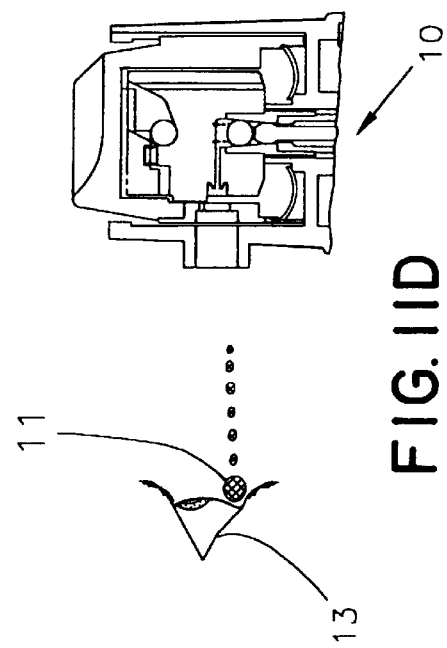
Figure 11C:
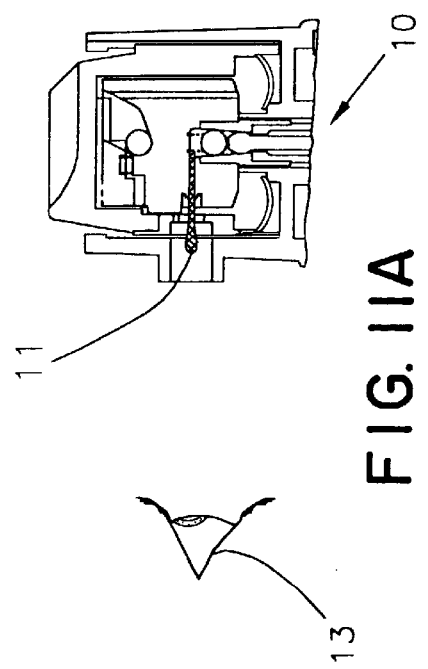
Figure 11D:
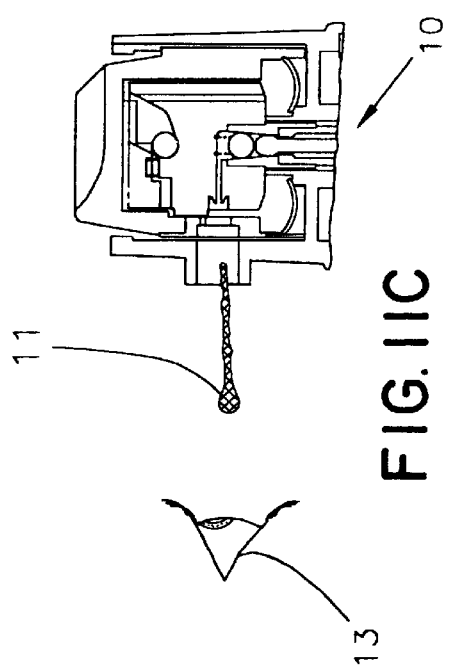

The actuator 20 is formed with a skirt 98 disposed between the dispensing cap 18 and the outer shell 30. Since the skirt 98 is not fixed to the dispensing cap 18 or the outer shell 30, the actuator 20 is capable of translating therebetween. Normally, the actuator 20 is biased away from the dispensing cap 18 by biasing means 100. Preferably, the biasing means 100 comprises a conventional coil spring but may also comprise spring member 100' disposed about the lower edge of the actuator, as shown in FIGS. 6, 9A and 9B. The spring member 100' is formed with a plurality of inwardly extending resilient spring fingers 101 which urge the actuator 20 away from the dispensing cap 18 when the spring fingers 101 are deformed against the bulkhead 34. Ridge 104 limits the upward travel of the actuator 20 and contains the actuator 20 within the pump body 14. A discharge aperture 106 is formed in the skirt 98 which is aligned to be juxtaposed with the dispensing aperture 36 and the discharge nozzle 86 when the actuator 20 is forced into contact with the dispensing cap 18, as shown in FIG. 3. The top of the actuator 108 is conveniently formed with an arcuate surface which can comfortably accommodate the tip of a finger of a user of the pump 10.

The inner surface of the actuator 110 and the upper surface of the dispensing cap 112 form a gravity sensitive failsafe mechanism for preventing the introduction of air into the inner chamber 48. An actuating block 114 extends from the inner surface 110 towards the upper surface of the dispensing cap 112. The upper surface 112 is formed with an arcuate slot 116 which accommodates ball 118. The slot 116 is formed to seat the ball 118 below the actuating block 114 when the sight 38 is directed at an angle, rotating clockwise, from approximately 155 degrees to 290 degrees, as shown in FIGS. 10A–D. Referring to FIG. 2, the lower surface of the slot 120 is formed at an angle α, which is preferably 110°, and the upper surface 122 is formed at angle β, measuring 25°. As the pump 10 is turned counterclockwise beyond 155 degrees, the ball 118 will slide up the upper surface 122 and no longer be in alignment with the actuating block 114. Similarly, if the pump 10 is rotated clockwise beyond 290 degrees, the ball 118 will roll up the lower surface 120 and out of alignment with the actuating block 114. The range of angles from 155 degrees to 290 degrees was chosen to ensure submersion of the end of the dip tube 54 within the liquid found in the reservoir 12 with fluid being present therein within predetermined levels.

Figure 8A:
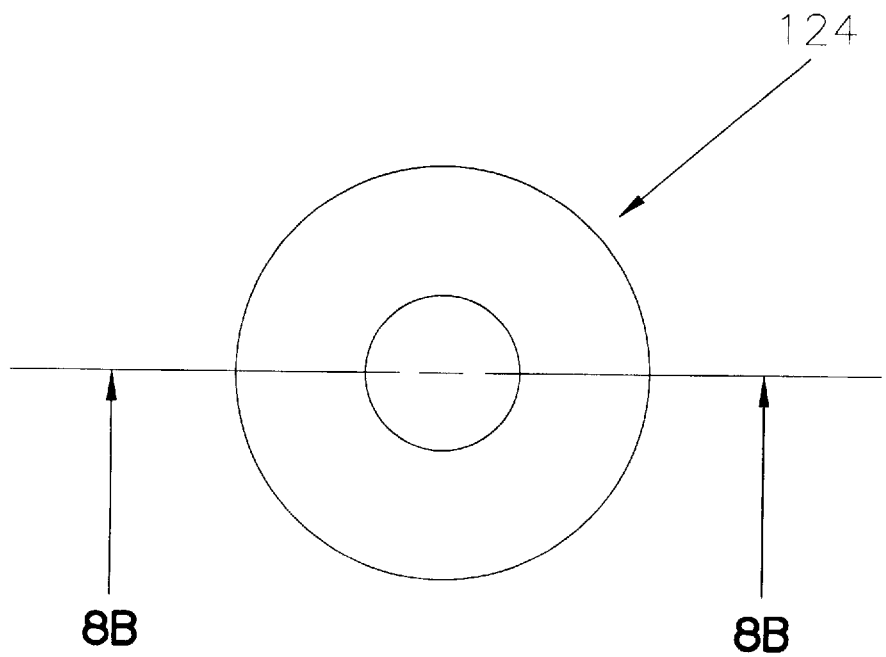
FIGS. 8A–B are respectively is a plan and cross-sectional side view of the latch of the new and improved pump of the subject invention.
Figure 8B:
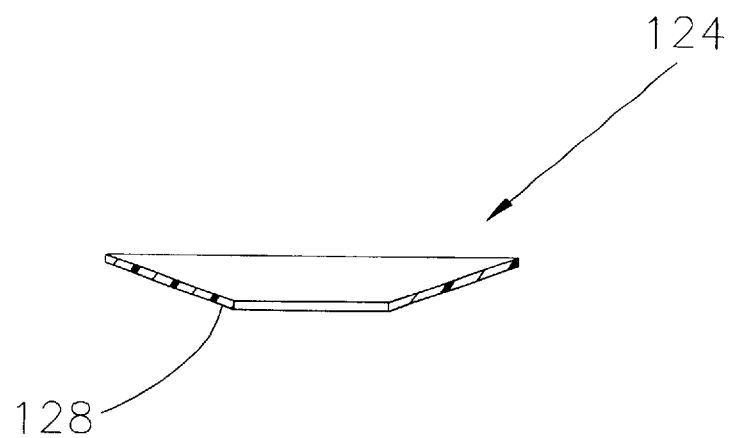

An annular, tapered latch 124, formed from a resilient plastic, preferably polypropylene, is disposed about the lower end of the actuator 126 about the inner body 32 and is shown in FIGS. 8A and 8B. The latch is formed with a bottom surface 128. An annular shoulder 130 extends from the bulkhead 34 forming a diameter larger than the inner opening of the latch 124. The actuator 20 is spaced from the dispensing cap 18 and may be pressed down without either the inner surface 110 or the actuating block 114 coming into contact with the dispensing cap 18, or the bottom surface 128 of the latch 124 touching the annular shoulder 130.

In operation, the reservoir 12 is filled with a fluid to a level below the vent 96 with the pump 10 being in a vertical position. Initially, the pump 10 must be primed with fluid being urged therethroughout. To do such priming, the pump 10 is activated several times using a normal pump operation. As fluid is drawn into the pump body 14, air will be expelled, with the pump 10 being primed when no air is within the dip tube 52, the pump body 14, or the dispensing cap 18. The pump process as described below is the same during priming, except the pump medium may include some air.

To dispense fluid from the pump 10, the actuator 20 is depressed into the pump body 14 with the bottom surface 128 of the latch 124 coming into contact with the annular shoulder 130, as shown in FIG. 3. The latch 124 freely deforms with further downward translation of the actuator 20. As the latch 124 continues to deform, the latch 124 generates resistance to further downward translation requiring increasing force to accomplish such translation. The force will eventually build up to a predetermined threshold force which overcomes the latch 124 and causes it to yield. As the threshold force is being reached, the actuating block 114 comes into contact with the ball 118. The threshold force necessary to overcome the latch 124 ensures the piston 56 will rapidly translate its full stroke. The resistance against downward translation can also be regulated through the size and quantity of the air vents 97. The depression of the actuator 20 causes the air in the void 90 to compress and requires additional force for further compression and further translation. Since the air vents 97 communicate with the atmosphere and the compressed air in the void 90 is bled thereto, having minimal or none of the air vents 97 results in a slow escape for the compressed air and resistance to translation of the actuator 20. An increase in the number or size of the air vents 97 allows the compressed air to escape quicker from the void 90 and reduce the resistance against downward translation. The combination of the latch 124 and the vents 97 can be manipulated to establish a threshold force required to operate the pump 10.

As shown in FIG. 3, the actuator 20 must translate the distance S1 for the actuating block 114 to come into contact with the ball 118. As the distance S1 is translated, the latch 124 and the air vents 97 offer resistance so that a threshold force must be applied to actuate the pump 10. With the distance S1 translated, the latch 124 will be on the verge of yielding under the threshold force and the ball 118 will be in contact with the actuating block 114. The distance S2 is equal to the stroke of the piston 56, and the actuator 20 and the dispensing cap 18 can only travel the distance S2 by having the latch 124 yield and the air of the void 90 overcome. With the application of the threshold force, the latch 124 is quickly deformed with the threshold force continuously being applied thereafter, thereby causing the actuator 20, along with the dispensing cap 18 and the piston 56, to quickly travel the distance S2.

Referring to FIG. 3, as the piston 56 travels downward the distance S2, fluid within the inner chamber 48 is compressed and forced through the annular flow path 70 about the head 72, which through the downward travel of the piston 56 is separated from the top of the piston 57. The fluid rushing past the head 72 will act against the outlet check valve element 82, with the pressure of the fluid eventually overcoming the bias of the quick return biasing means 84 and causing the outlet check valve element 82 to separate from the tapered portion 78. In turn, the fluid travelling past the outlet check valve element 82 will force fluid into the discharge nozzle 86 and the microdose 11 out of the nozzle 86, which is aligned with the discharge aperture 106 and the dispensing aperture 36. Due to the threshold force required to overcome the latch 124 and the air of the void 90, the downward travel of the piston 56, through the distance S2, is rapid, resulting in a rapid surge of fluid through the nozzle 86. The microdose 11 exiting from the discharge nozzle 86 will form a non-aerosolized jet stream as shown in FIGS. 11A–D. Due to the surface tension of fluid, as the microdose 11 travels away from the pump 10, it will tend to break into a series of drops with a relatively large droplet and several smaller droplets, which will all hit the eye 13 nearly simultaneously.

Figure 4:
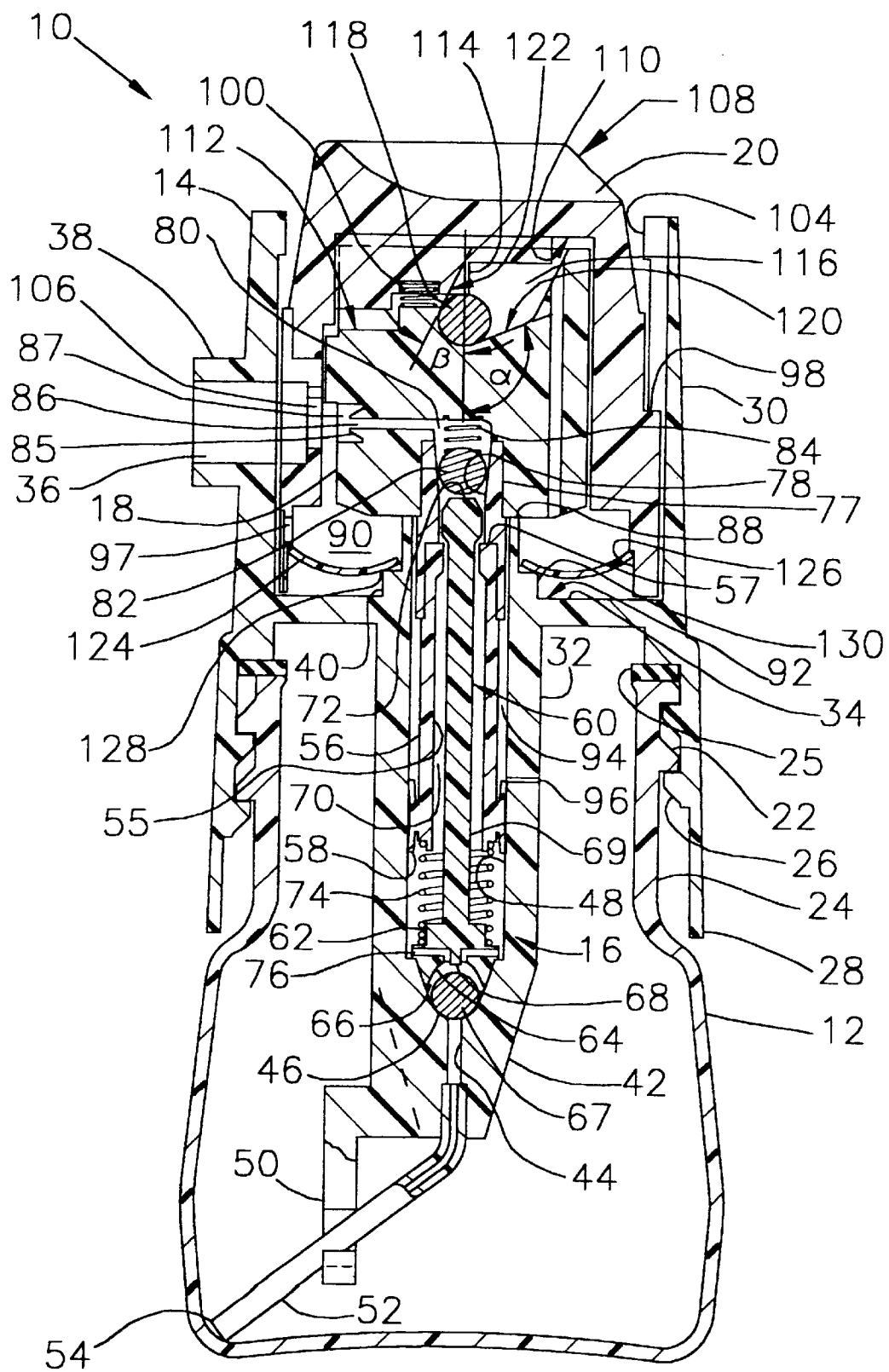
FIG. 4 is a cross-sectional view of the new and improved pump of the subject invention returning to an unactuated position.
Figure 5:
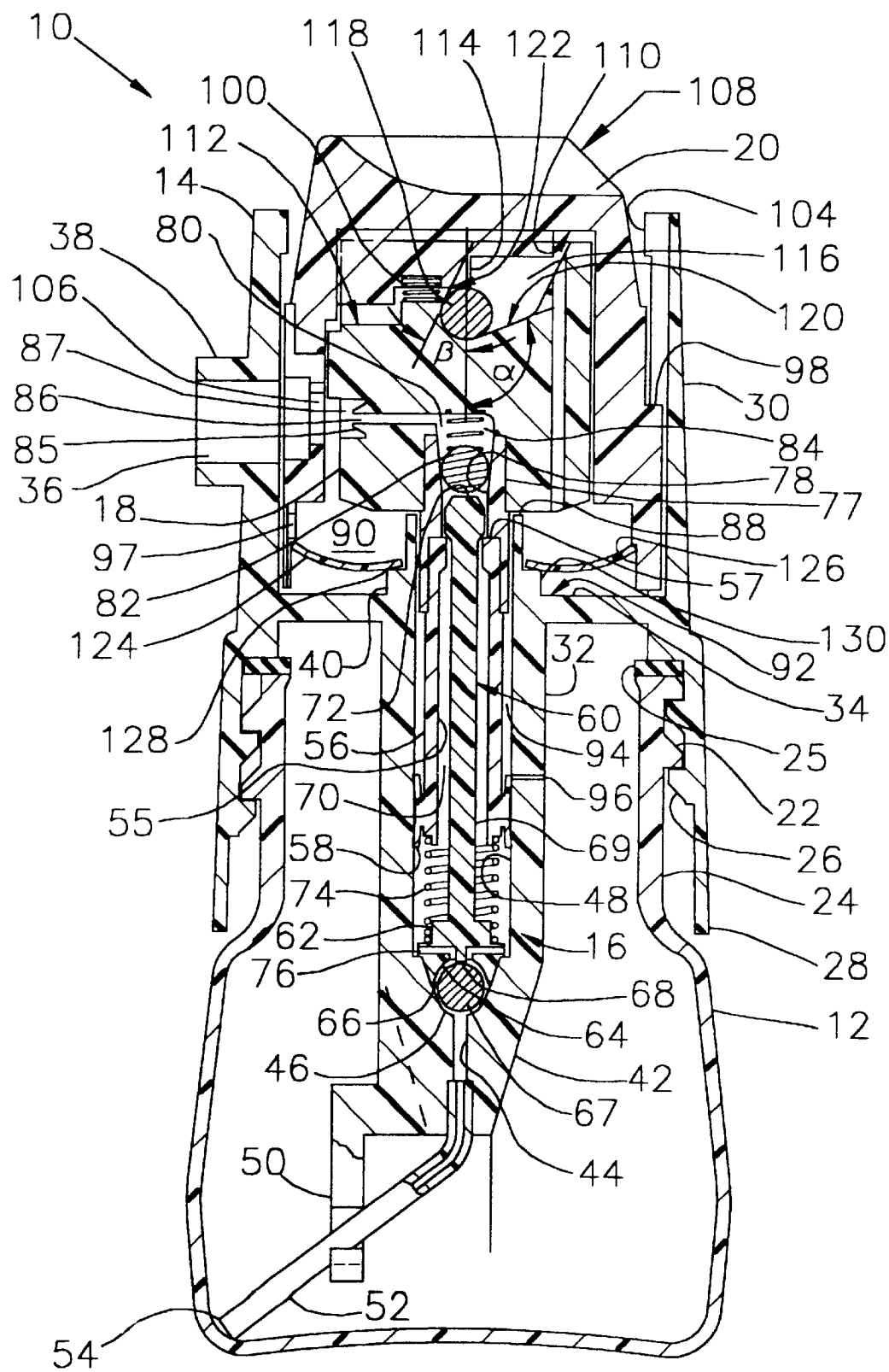
FIG. 5 is a cross-sectional view of the new and improved pump of the subject invention drawing fluid therein.

The yielding of the latch 124 will cause the fluid to surge past the head 72 and the outlet check valve element 82. As shown in FIG. 4, the quick return biasing means 84 will urge the outlet check valve element 82 into contact with the tapered portion 78, once the surge of fluid has bypassed the outlet check valve element 82. The piston spring 74 will urge the piston 56, the dispensing cap 18 and the actuator 20 upwards, with the biasing means 100 further urging the actuator 20 away from the dispensing cap 18. Simultaneously, the latch 124 will separate from the annular shoulder 130 and resume its undeformed, annular tapered form. The upward travel of the piston 56 increases the volume of the inner chamber 48 and creates a suction effect. As a result, the inlet check valve element 67 is drawn towards the inner chamber 48 and into contact with the protrusion 68, as depicted in FIG. 5. Fluid is then drawn from the dip tube 52 through the inlet channel 44, the inlet chamber 66 and the ports 76 into the inner chamber 48. As the inner chamber 48 fills with the drawn fluid, pressure increases therein and the inlet check valve element 67 is forced into a seated position in the seat 46.

The pump 10 can be manually actuated without the latch 124. The latch 124, however, ensures the application of the threshold force, which, in turn, ensures the application of a full dose in a jet stream, as described above.

Simultaneous to the pumping operation, the vent 96 is exposed to the annular air chamber 94 with the downward travel of the piston 56 and to ambient conditions. As such, the pressure on the surface of the fluid in the reservoir 12 is restored to atmospheric with each actuation of the pump 10.

As is readily apparent, numerous modifications and changes may readily occur to those skilled in the art, and hence it is not desired to limit the invention to the exact construction and operation shown and described, and accordingly all suitable modification equivalents may be resorted to falling within the scope of the invention as claimed.

What is claimed is:

1. A microdispensing pump for administering minute doses of fluid, said pump comprising:

a pump body formed to define an inner chamber and an inlet chamber with a protrusion extending therein, said inner chamber being in communication with said inlet chamber;

a pump means for urging the fluid through said pump body, said pump means being disposed within said inner chamber; and an inlet check valve element disposed within said inlet chamber opposite said protrusion, wherein said inlet check valve element regulates the flow of the fluid into the inner chamber and wherein said protrusion limits the movement of said inlet check valve element within said inlet chamber such that a swept volume of said inlet check valve element is less than the volume of the minute dose of fluid.

2. A pump as in claim 1, wherein said inlet chamber has an inner surface formed to substantially define a sphere.

3. A pump as in claim 1, further comprising a dispensing cap extending from said pump means formed to define an outlet chamber with an inlet which communicates with said inner chamber and an outlet check valve element disposed within said outlet chamber which is urged into sealing contact with said inlet of said dispensing cap by a quick return biasing means selected from the group consisting of a resilient rubber ball, a coil spring, and a leaf spring.

4. A microdispensing pump for administering minute doses of fluid, said pump comprising:

a pump body formed to define a hollow inner chamber;

a pump means for drawing fluid into said pump body and urging the fluid therethrough, said pump means being disposed within said inner chamber;

a dispensing cap extending from said pump means formed to define an outlet chamber with an inlet which communicates with said inner chamber, said dispensing cap having an outer surface and a slender discharge nozzle communicating said outer surface with said outlet chamber;

an outlet check valve element disposed within said outlet chamber for controlling flow of the fluid into the outlet chamber; and a quick return biasing means for urging said outlet check valve element into sealing contact with said inlet of said dispensing cap as the pump means draws the fluid into said pump body.

5. A pump as in claim 4, wherein said quick return biasing means is selected from the group consisting of a resilient rubber ball, a coil spring, and a leaf spring.

6. A microdispensing pump for administering minute doses of fluid, said pump comprising:

a pump body having an inner body being formed to define a hollow inner chamber, an opened upper end and a lower end, with said lower end being formed to define an inlet aperture and inlet valve seat;

a pump mechanism disposed within said pump body having a cylindrical piston slidably and sealingly supported within said inner body, an elongated poppet with a base mounted over the inlet valve seat, a stem extending from said base through said piston in a spatial relationship and a head depending from said stem, said cylindrical piston having an inner surface defining a diameter, said head having a diameter greater than the diameter of said inner surface, and a biasing means for urging said piston into sealing contact with said head of said poppet, wherein the base forms a substantially spherical inlet chamber with the inlet valve seat, at least one port being formed in said base for communicating said inlet chamber with said inner chamber, and a protrusion extending from said base into said inlet chamber;

an inlet check valve element disposed within said inlet chamber for controlling flow of the fluid into the inner chamber whereby said protrusion limits the movement of said inlet check valve element;

a dispensing cap extending from said piston and disposed within said pump body, said dispensing cap formed to define an outlet chamber with an inlet which communicates with said inner chamber when said poppet is not in sealing contact with said piston, and said dispensing cap having an outer surface and a slender discharge nozzle communicating said outer surface with said outlet chamber; and an outlet check valve element disposed within said outlet chamber for controlling flow of the fluid into the outlet chamber, said outlet check valve element being urged into sealing contact with said inlet of said dispensing cap by a quick return biasing means as the pump administers the minute dose of fluid, whereby force applied to said dispensing cap causes said piston to slide within said cylinder and urge the fluid through said pump mechanism and said nozzle.

7. A pump as in claim 6, further comprising an actuator slidably disposed in said pump body, said actuator having an annular deformable latch mounted thereto with the inner periphery of the latch being unfixed.

8. A pump as in claim 7, further comprising an actuator biasing means for urging the actuator away from said dispensing cap.

9. A pump as in claim 6, further comprising a dip tube for communicating fluid between the reservoir and the inlet aperture of the pump body, said dip tube formed to define a substantially cylindrical passageway which encompasses less volume than the minute dose of fluid.

10. A pump as in claim 9, wherein said pump body further comprises a hook means for securing said dip tube in a predetermined position.

11. A pump as in claim 6, wherein said quick return biasing means is selected from the group consisting of a resilient rubber ball, a coil spring, and a leaf spring.

12. A pump as in claim 6, wherein said pump body includes a substantially cylindric outer shell formed to define a dispensing aperture juxtaposed with said nozzle.

13. A pump as in claim 12, wherein a sight is formed about the dispensing aperture of said pump body.

14. A pump as in claim 6, wherein said outer surface of said dispensing cap is formed to define a conical rim about said discharge nozzle.

15. A pump as in claim 13, wherein said outer surface of said dispensing cap forms an annular depression about said conical rim.

16. A pump as in claim 6, wherein said discharge nozzle has a length to throat ratio of approximately 7 to 1.

17. A pump as in claim 6, wherein said protrusion is formed to define a swept volume of said inlet check valve element less than the volume of the minute dose of fluid.

18. A microdispensing pump with a discharge aperture for administering minute doses of fluid with the discharge aperture being oriented within an angular operating range, said pump comprising:

a dispensing cap formed about an axis having an outer surface formed to define the discharge aperture, said dispensing cap also formed to define an outlet chamber and a discharge nozzle communicating said outlet chamber with the discharge aperture, and said outer surface also being formed to define a slot;

a pump means for delivering fluid to said dispensing cap, said pump means communicating with said outlet chamber;

an actuator disposed about said axis having an inner actuating surface facing said dispensing cap with an actuating member extending therefrom, said actuating member being aligned with at least a portion of said slot, said actuator capable of translation along said axis; and a failsafe ball disposed within said slot, wherein said ball is aligned with said actuating member where the discharge aperture is oriented within the operating range.

19. A pump as in claim 18, wherein said slot is formed with a first surface defining an acute angle of 25° relative to said axis and a second surface defining an obtuse angle of 110° relative to said axis.

20. A pump as in claim 18, further comprising an annular deformable latch mounted to said actuator with an unfixed inner periphery.

21. A pump as in claim 18, further comprising an actuator biasing means for urging said actuator from said dispensing cap.

22. A pump as in claim 18, further comprising a dip tube for communicating the fluid to the pump means formed to define a substantially cylindrical passageway encompassing less volume than the minute dose of fluid.

23. A pump as in claim 18, further comprising at least one check valve means for controlling the flow of the fluid through said pump means.

24. A microdispensing pump for administering minute doses of fluid within an angular operating range, said pump comprising:

a reservoir having a closed bottom for accommodating the fluid and an opened top defining a neck;

a pump body having a substantially cylindrical outer shell with an opened upper portion formed to define a dispensing aperture and a lower portion disposed about said neck, a substantially cylindric inner body disposed co-axially within said outer shell and a transverse annular bulkhead joining said outer shell and said inner body, said inner body being formed to define a hollow cylindrical inner chamber, an opened upper end and a lower end, with said lower end being formed to define an inlet aperture and inlet valve seat;

a pump mechanism disposed within said pump body having a cylindrical piston slidably and sealingly supported within said inner body, an elongated poppet with a base mounted over the inlet valve seat, a stem extending from said base through said piston in a spatial relationship and a head depending from said stem, said cylindrical piston having an inner surface defining a diameter, said head having a diameter greater than the diameter of said inner surface, and a biasing means provided to urge said piston into sealing contact with said head of said poppet, wherein the base forms a substantially spherical inlet chamber with the inlet valve seat, at least one port being formed in said base for communicating said inlet chamber with said inner chamber, and a protrusion extending from said base into said inlet chamber;

an inlet check valve element disposed within said inlet chamber for controlling flow of the fluid into the inner chamber whereby said protrusion limits the movement of said inlet check valve element;

an actuator slidably disposed in the upper portion of the outer shell, said actuator having an inner actuating surface facing said inner body with an actuating member extending therefrom;

a dispensing cap extending from said piston and disposed within said upper portion of said pump body between said actuator and said inner body, said dispensing cap formed to define an outlet chamber with an inlet which communicates with said inner chamber when said poppet is not in sealing contact with said piston, said dispensing cap having an outer surface and a slender discharge nozzle communicating said outer surface with said outlet chamber, said nozzle being juxtaposed with said dispensing aperture of said pump body, and said dispensing cap having an upper surface facing said inner actuating surface formed to define a slot, a portion of said slot being aligned with said actuating member;

a failsafe ball disposed within said slot, wherein said ball being aligned with said actuating member where the pump is oriented within the operating range; and an outlet check valve element disposed within said outlet chamber for limiting flow of the fluid into the outlet chamber, said outlet check valve element being urged into sealing contact with said inlet of said dispensing cap by a quick return biasing means as the pump administers the minute dose of fluid, whereby force applied to said actuator is transferred to said dispensing cap through said actuating member and said failsafe ball with the pump being oriented within the operating range and whereby said dispensing cap causing said piston to slide within said cylinder and urge the fluid through said pump mechanism and said nozzle.

25. A pump as in claim 24, wherein said slot is formed with a first surface defining an acute angle of 25° relative to said axis of said pump body and a second surface defining an obtuse angle of 110° relative to said axis of said pump body.

26. A pump as in claim 24, further comprising a dip tube for communicating the fluid between said reservoir and said inlet aperture of said inner body, said dip tube formed to define a substantially cylindrical passageway which encompasses less volume than the minute dose of fluid.

27. A pump as in claim 26, wherein said pump body further comprises a hook means for securing said dip tube in a predetermined portion.

28. A pump as in claim 24, wherein an annular deformable latch with an unfixed inner periphery is mounted to said actuator and disposed between said dispensing cap and said bulkhead.

29. A pump as in claim 24, further comprising an actuator biasing means for urging said actuator from said dispensing cap.

30. A pump as in claim 24, wherein said quick return biasing means is selected from the group consisting of a resilient rubber ball, a coil spring and a leaf spring.

31. A pump as in claim 24, wherein said outer surface of said dispensing cap is formed to define a conical rim about said discharge nozzle.

32. A pump as in claim 31, wherein said outer surface of said dispensing cap forms an annular depression about said conical rim.

33. A pump as in claim 24, wherein said discharge nozzle has a length to throat ratio of 7 to 1.

34. A pump as in claim 24, wherein said protrusion is formed to define a swept volume of said inlet check valve element less than the volume of the minute dose of fluid.

35. A microdispensing pump for repeatedly administering a predetermined minute dose of fluid, said pump comprising:

a pump body formed with a hollow inner chamber;

pump means for urging the predetermined dose of fluid through said pump body;

an actuator mounted on said pump means for actuating said pump means; and resistance means for creating a predetermined amount of resistance to the actuating of said pump means by said actuator, wherein said resistance means includes a deformable latch, whereby a force sufficient to administer the predetermined dose of fluid is required to overcome the predetermined amount of resistance.

* * * * *